United States Patent
Miyajima et al.

(10) Patent No.: US 10,521,907 B2
(45) Date of Patent: Dec. 31, 2019

(54) IMAGE PROCESSING APPARATUS, PROGRAM, AND RADIATION IMAGE CAPTURING APPARATUS

(71) Applicant: Shimadzu Corporation, Kyoto (JP)

(72) Inventors: Takahiro Miyajima, Kyoto (JP); Junya Yamamoto, Kyoto (JP); Kazuyoshi Nishino, Kyoto (JP)

(73) Assignee: Shimadzu Corporation, Nakagyo-ku, Kyoto-shi, Kyoto (JP)

( * ) Notice: Subject to any disclaimer, the term of this patent is extended or adjusted under 35 U.S.C. 154(b) by 169 days.

(21) Appl. No.: 15/927,673

(22) Filed: Mar. 21, 2018

(65) Prior Publication Data

US 2019/0295247 A1  Sep. 26, 2019

(51) Int. Cl.

| G06K 9/00 | (2006.01) |
|---|---|
| G06T 7/00 | (2017.01) |
| G06T 7/12 | (2017.01) |
| G06T 7/73 | (2017.01) |
| G06T 5/00 | (2006.01) |
| A61B 6/12 | (2006.01) |
| A61N 1/362 | (2006.01) |

(52) U.S. Cl.
CPC .............. *G06T 7/0012* (2013.01); *A61B 6/12* (2013.01); *G06T 5/008* (2013.01); *G06T 7/12* (2017.01); *G06T 7/74* (2017.01); *A61N 1/362* (2013.01); *G06T 2207/10116* (2013.01); *G06T 2207/20132* (2013.01); *G06T 2207/30061* (2013.01)

(58) Field of Classification Search
CPC combination set(s) only.
See application file for complete search history.

(56) References Cited

U.S. PATENT DOCUMENTS

| 2001/0024516 A1* | 9/2001 | Yoshioka | A61B 8/08 |
|---|---|---|---|
| | | | 382/128 |
| 2007/0086641 A1* | 4/2007 | Nakamura | G06T 7/0012 |
| | | | 382/132 |
| 2010/0322493 A1* | 12/2010 | Wei | G06T 7/0014 |
| | | | 382/128 |
| 2015/0310299 A1* | 10/2015 | Goto | G01R 33/543 |
| | | | 382/128 |
| 2015/0310625 A1* | 10/2015 | Shimamura | A61B 6/4233 |
| | | | 382/132 |

FOREIGN PATENT DOCUMENTS

JP    2015-100593 A    6/2015

* cited by examiner

*Primary Examiner* — Alex Kok S Liew
(74) *Attorney, Agent, or Firm* — Muir Patent Law, PLLC

(57) ABSTRACT

The apparatus is equipped with an intersection identification unit configured to generate a pixel value profile which is a profile indicating relevance between a position of each pixel in a pixel array crossing a contour and a lung field of a subject and a corresponding pixel value and a moving average profile which is a profile indicating relevance between the position of each target pixel and a moving average of a corresponding pixel value and search an intersection of both the profiles located at a position where the pixel value profile surpasses the moving average profile from a direction from a rear end to a front end of the pixel array.

6 Claims, 15 Drawing Sheets

X-ray image (original image P0)

Radiation image
(Original image)

IMAGE PROCESSING APPARATUS, PROGRAM, AND RADIATION IMAGE CAPTURING APPARATUS

TECHNICAL FIELD

The present invention relates to an image processing apparatus for improving visibility of a part of a radiation image, a program, and a radiation image capturing apparatus.

BACKGROUND ART

FIG. 22 illustrates a radiation image captured by a radiation image capturing apparatus. In the case of observing a lung field of a subject reflected in such a radiation image, it is necessary to perform image processing to improve the visibility of the lung field by adjusting the contrast of the lung field.

In a radiation image, various portions of a subject such as a bony part other than a lung field are reflected. A bony part of a subject is darkly reflected in a radiation image because the bony part hardly transmits radiation. Furthermore, the portion outside the contour of the subject reflected in the radiation image is a portion not reflecting the subject but a portion reflecting the air. The portion not reflecting the subject is brightly reflected in the radiation image because there is nothing to transmit radiation. In the radiation image, the lung field is brighter than the bony part of the object but darker than the portion outside the contour of the subject which is a portion reflecting the air.

The lung field of the radiation image totally looks to be filled with a gray color with poor contrasting density. This is because the pixels located in the lung field reflected in the radiation image have similar pixel values.

When a contrast adjustment is executed for the entire radiation image to increase the visibility of the lung field, the contrast adjustment is also executed for the portions of the radiation image in which the bony part and the air are reflected. Although such a contrast adjustment may increase the visibility of the radiation image as a whole, as far as the lung field is concerned, there is not so much improvement in visibility. The lung field after the contrast adjustment is still totally poor in contrasting density because of the following reasons. That is, in the case of expressing the contrast of the lung field, low pixel values are used to express bony parts of a subject, and high pixel values are used to express the portion where the air is reflected. Therefore, the lung field should be expressed with the remaining moderate pixel values.

Under the circumstances, a method of making a contrast adjustment only on a lung field in a radiation image has been conventionally conceived. According to this method, since the lung field can be expressed with more various color tones, the visibility of the lung field can be assuredly increased. The method is intended to execute trimming for extracting a lung field in a radiation image and make a contrast adjustment on the trimmed image in which the lung field is enlarged. In the trimmed image, dark portions reflecting bony parts of a subject and bright portions reflecting the air are excluded, so the trimmed image is not affected by these portions.

A conventional lung field trimming method will be described. In a conventional method, first, the edge enhancement processing is performed on a radiation image as shown in FIG. 23. The edge enhancement processing is image processing that can be realized by spatial processing such as differentiation processing and enhances the darkness of the portions where the pixel value in the image changes extremely. With this edge enhancement processing, the contour of the subject can be grasped. The edge enhancement is detailed in Patent Document 1.

According to the conventional method, the trimming processing of cutting out the region including a lung field as shown in FIG. 24 is performed based on the contour of the subject. In the trimming processing at this time, the lung field region is recognized based on the edge enhanced image, and the lung field including its periphery is roughly cut out from the radiation image.

Subsequently, the contour of the lung field is searched from the trimmed image as shown in FIG. 25. Searching the contour of the lung field is relatively easy since the trimmed image reflects almost only the lung field. In this way, the visibility of the lung field is improved. As described above, the recognition of the contour of the lung field is executed in two stages.

By performing the contrast adjustment only on the lung field surrounded by the searched lung field contour, the accuracy of the lung field can be assuredly improved.

PRIOR ART

Patent Document

Patent Document 1: Japanese Unexamined Patent Application Publication No. 2015-100593

SUMMARY OF THE INVENTION

Problems to be Solved by the Invention

However, conventional image processing has the following problems. That is, according to the conventional configuration, a false recognition of the lung field contour occurs, which results in a failure of the trimmed image generation processing (first stage of the lung field recognition) described with reference to FIG. 24.

In a conventional image processing using an edge enhanced image, a subject image is predicted, and based on this prediction, the trimming of the peripheral portion of the lung field is performed. Therefore, according to a conventional method, the operation can be performed normally with respect to a radiation image reflecting a normal subject image.

However, in a conventional configuration, if an unexpected image is reflected in a radiation image, a false recognition of a contour of a lung field is likely to occur. An unexpected image denotes, for example, a projection image of a cardiac pacemaker embedded in a subject as shown in a radiation image in FIG. 26. A cardiac pacemaker contains metal which is reflected relatively dark in a radiation image. A cardiac pacemaker is usually reflected in such a manner as to be overlapped with a lung field.

When edge enhancement processing is performed on such a radiation image, the contour of the cardiac pacemaker is emphasized as shown in FIG. 26. In a conventional method, in cases where a cardiac pacemaker is reflected in a radiation image, there is a false recognition that this portion is a contour of a subject. As a result, a trimmed image in which a part of the lung field is cut out as shown in FIG. 27 is generated. It is impossible to get the contour of the entire lung field from such a trimmed image.

In addition, in cases where an annotation is reflected in a radiation image, the trimming of the radiation image will not be performed correctly. The aforementioned annotation denotes a letter, such as, e.g., "R", added by composition in the upper portion of the radiation image obtained by image capturing as shown in FIG. 28. Such an annotation is normally reflected outside a lung field.

When edge enhancement processing is performed on such a radiation image, the contour of the annotation will be emphasized as shown in FIG. 28. In a conventional method, in cases where an annotation is reflected in a radiation image, there occurs a false recognition that this portion is a contour of a subject, and a trimmed image including a portion outside a contour of a subject is generated as shown in FIG. 29. It is difficult to accurately obtain a contour of a lung field from such a trimmed image.

The present invention was made in view of the aforementioned circumstances, and its object is to provide an image processing apparatus capable of assuredly improving visibility of a lung field by assuredly recognizing a position of a lung field reflected in a radiation image.

Means for Solving the Problems

In order to solve the aforementioned problems, the present invention has the following configuration.

That is, the image processing apparatus according to the present invention is an image processing apparatus for applying a luminance adjustment to a lung field corresponding portion of a radiation image reflecting a contour of a subject. The image processing apparatus includes: a pixel value profile generation means configured to generate a pixel value profile which is a profile indicating relevance between a position of each pixel in a pixel array crossing the contour of the subject and the lung field and a corresponding pixel value; a moving average profile generation means configured to generate a moving average profile which is a profile indicating relevance between a position of each target pixel and a moving average of a corresponding pixel value by setting a pixel group having a head of the pixel array facing a front end which is a contour side of the subject and a tail of the pixel array facing a rear end side which is a lung field side, setting the target pixel among the pixel group positioned at a head portion, calculating the moving average of the pixel value of the target pixel by averaging the pixel values of pixels constituting the pixel group, and thereafter successively calculating the moving average of the pixel value corresponding to the target pixel while moving the pixel group on the pixel array; an intersection identification means configured to identify an intersection located closest to a front end side of the pixel array among intersections different in derived pixel array by searching an intersection located closest to the rear end side of the pixel array among intersections of the two profiles appearing at a position where the pixel value profile surpasses the moving average profile from a direction from a rear end of the pixel array to a front end of the pixel array, and executing a search operation for a plurality of pixel arrays arranged in parallel with each other; a trimming means configured to execute trimming for extracting the lung field together with a peripheral portion thereof from the radiation image by recognizing a position of the peripheral portion of the lung field based on a position of the contour of the subject based on a searched intersection; and a lung field contour extraction means configured to extract the contour of the lung field reflected in a trimmed image generated by the trimming means.

[Functions and Effects] According to the present invention, it is possible to provide an image processing apparatus capable of assuredly improving visibility of a lung field by assuredly recognizing a position of a lung field reflected in a radiation image. That is, in the configuration of the present invention, it is provided with an intersection identification means configured to generate a pixel value profile which is a profile indicating relevance between a position of each pixel in a pixel array crossing a contour and a lung field of a subject and a corresponding pixel value and a moving average profile which is a profile indicating relevance between a position of each target pixel and a moving average of a corresponding pixel value and search an intersection of both profiles located at a position where the pixel value profile surpasses the moving average profile from a direction facing from a rear end toward a front end in the pixel array (direction from the lung field side toward the contour side of the subject). It is highly probable that the intersection indicates a contour position of a subject.

In the present invention, even in cases where an annotation is reflected in a radiation image, a contour of a subject can be accurately identified. This is because the intersection identification means is configured to search the intersection located closest to the rear end side of the pixel array among intersections which meet the condition. Since the contour of the subject is positioned on the rear end side of the pixel array than the annotation, it can be judged that the intersection located closest to the rear side among intersections which meet the condition is related to the contour.

In the present invention, even in cases where an image of a cardiac pacemaker is reflected in a radiation image, a contour of a subject can be accurately identified. This is because the intersection identification means executes an intersection search operation on a plurality of pixel arrays extending in parallel with each other to obtain an intersection corresponding to each pixel array to thereby identify an intersection positioned closest to the front end side of the pixel array among intersections. The pixel arrays include a pixel array crossing the pacemaker image and a pixel array not crossing the pacemaker image. From the pixel array crossing the pacemaker image, an intersection is found at the boundary between the lung field and the pacemaker image, and from the pixel array not crossing the pacemaker image, an intersection is found at the contour position of the subject. These intersections include an intersection positioned on the front end side of the pixel array and an intersection positioned on the rear end side of the pixel array. Since the pacemaker image is positioned on the rear end side of the pixel array than the contour of the subject, the intersection positioned on the rear end side of the pixel array is considered to be positioned at the boundary between the lung field and the pacemaker image. According to the present invention, since the intersection positioned closest to the front end side of the pixel array among the intersections operates as an intersection indicating the position of the contour of the subject, the boundary between the lung field and the pacemaker image will not be mistakenly recognized as the contour of the subject.

When the contour of the subject can be extracted, the image processing for extracting the entire lung field from the radiation image can be assuredly performed, which in turn can assuredly improve the visibility of the lung field.

Further, in the aforementioned image processing apparatus, it is preferable that the trimming means operate by setting a position on the radiation image shifted from the intersection toward the front end side of the pixel array by a predetermined width to an image cutting out position.

[Functions and Effects] The aforementioned configuration represents a more desirable configuration of the image processing apparatus of the present invention. This is because the intersection tends to deviate toward the rear end side than the contour of the subject.

Further, in the aforementioned image processing apparatus, it is more preferable that the moving average profile generation means generate the moving average profile while moving the pixel group from the rear end of the pixel array toward the front end thereof.

[Functions and Effects] The aforementioned configuration represents a more desirable configuration of the image processing of the present invention. By configuring as described above, the generation of the profile can be preferentially performed on the relatively necessary portion among profiles.

Further, in the aforementioned image processing apparatus, it is more preferable that the intersection identification means repeatedly execute an intersection search every time the intersection identification means calculate the moving average of the pixel value and the moving average profile generation means complete generation of the moving average profile when the intersection identification means completes the intersection searching.

[Functions and Effects] The aforementioned configuration represents a more desirable configuration of the image processing of the present invention. By configuring as described above, the operational cost of the moving average profile generation means can be reduced.

Effects of the Invention

According to the present invention, it is possible to provide an image processing apparatus capable of assuredly improving visibility of a lung field by assuredly recognizing a position of a lung field reflected in a radiation image. That is, the configuration of the present invention is provided with an intersection identification means configured to generate a pixel value profile which is a profile indicating relevance between a position of each pixel in a pixel array crossing a contour and a lung field of a subject and a corresponding pixel value and a moving average profile which is a profile indicating relevance between a position of each target pixel and a moving average of a corresponding pixel value, and search an intersection of both profiles located as a position where the pixel value profile surpasses the moving average profile from a direction facing from a rear end toward a front end in the pixel array (direction from the lung field side toward the contour side of the subject).

EMBODIMENTS FOR CARRYING OUT THE INVENTION

First Embodiment

Figure 1:
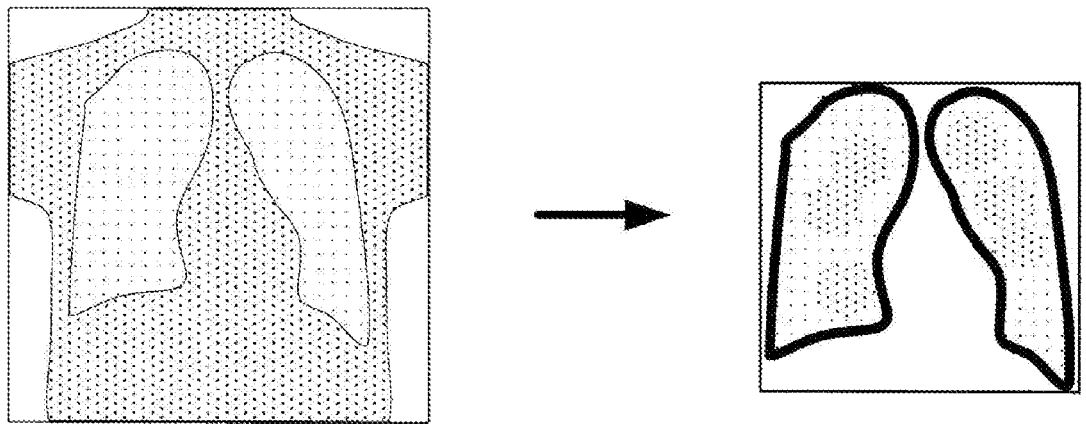
FIG. 1 is a schematic diagram illustrating image processing which is performed by an image processing apparatus according to a first embodiment.

Next, some embodiments according to the present invention will be described. As shown in FIG. 1, an image processing apparatus according to the present invention is configured such that when a chest X-ray image (original image P0) of a subject captured by an X-ray image capturing apparatus is input, an image in which the contrast of the subject's lung field is adjusted is outputted.

Figure 2:
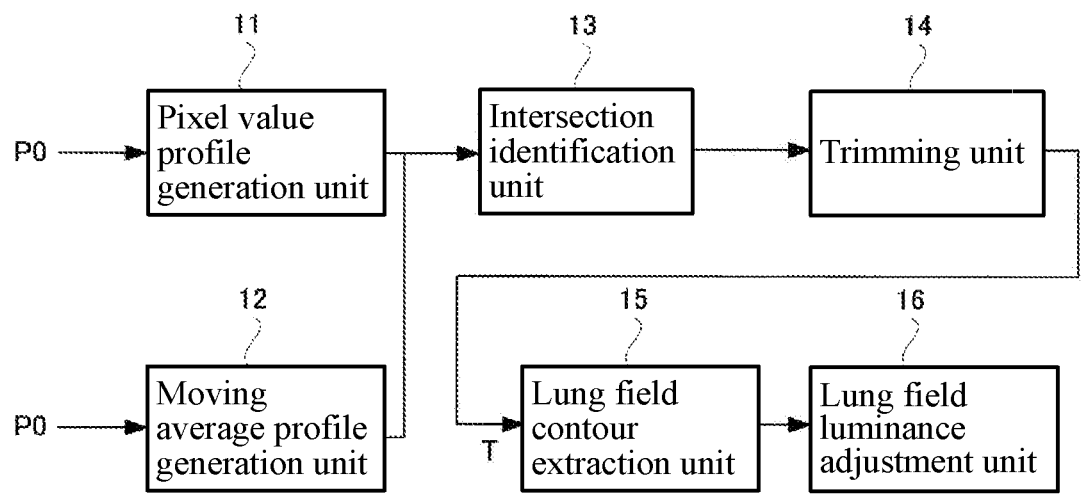
FIG. 2 is a functional block diagram illustrating a configuration of the image processing apparatus according to the first embodiment.

FIG. 2 is a functional block diagram showing the entire image processing performed by the image processing apparatus 1. As shown in FIG. 2, a pixel value profile generation unit 11, a moving average profile generation unit 12, and an intersection identification unit 13 identify a rough position of a lung field on the original image P0, and a trimming unit 14 generates a trimmed image T in which the lung field is extracted from the original image P0 together with the peripheral region. The lung field contour extraction unit 15 recognizes the lung field region on the trimmed image and identifies the contour of the lung field. A lung field luminance adjustment unit 16 adjusts the contrast inside the contour of the lung field. As described above, the image processing apparatus according to the present invention is configured to perform the contrast adjustment only on the lung field of the original image P0.

The pixel value profile generation unit 11 corresponds to the pixel value profile generation means of the present invention, and the moving average profile generation unit 12 corresponds to the moving average profile generation means of the present invention. The intersection identification unit 13 corresponds to the intersection identification means of the present invention, and the trimming unit 14 corresponds to the trimming means of the present invention. The lung field contour extraction unit 15 corresponds to the lung field contour extraction means of the present invention.

Therefore, in the image processing apparatus 1 of the present invention, the first stage of the lung field recognition is executed by the pixel value profile generation unit 11, the moving average profile generation unit 12, the intersection identification unit 13, and the trimming unit 14, and the second stage of the lung field recognition is executed by the lung field contour extraction unit 15. The present invention aims to solve the problem in the first stage of the lung field recognition in a conventional configuration, and therefore the configuration of each of the aforementioned units 11, 12, 13, and 14 is the features of the present invention.

That is, in a conventional configuration, the first stage of the lung field recognition was performed by subjecting the original image to the edge enhancement processing. On the other hand, the present invention is configured to execute the first stage of the lung field recognition by comparing two profiles. The units 11, 12, 13, and 14 collaboratively find a contour of a subject on a shoulder portion of the subject, and execute the cutting of the original image P0 at this portion to prevent the portion reflecting the air above the original image P0 from taking into the trimmed image including a lung field. Hereinafter, the operation of each of the units 11, 12, 13, and 14 will be described.

Figure 3:
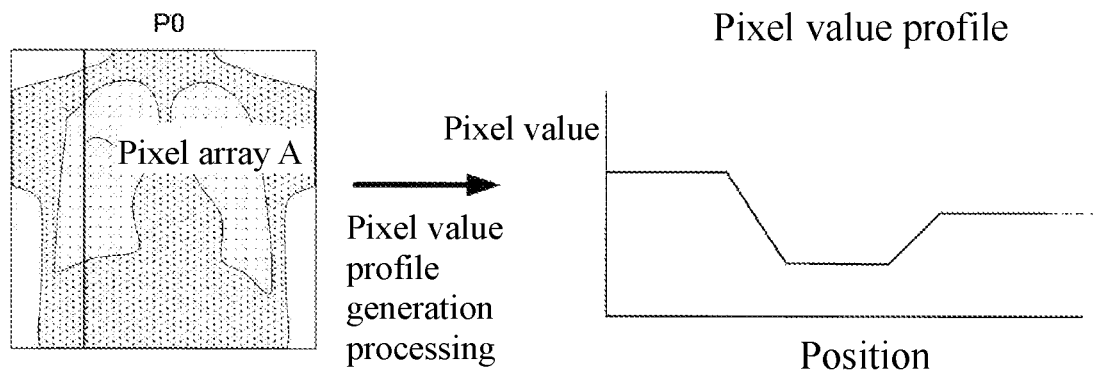
FIG. 3 is a schematic diagram illustrating pixel value profile generation processing according to the first embodiment.

FIG. 3 shows the operation of the pixel value profile generation unit 11. The pixel value profile generation unit 11 sets a pixel array A in which pixels are arranged in a row in a vertical direction in the original image P0. This pixel array A extends so as to cross the contour of the subject and the lung field. The upper end portion thereof is a portion of the original image P0 where the air is reflected, the central portion thereof is a portion where the lung field is reflected, and the portion between the two portions is a portion where the subject's shoulder is reflected. Pixels belonging to each portion are different in brightness. In general, the portion where the air is reflected is the brightest portion, and the portion where the lung field is reflected is the next brightest portion. The portion where the shoulder is reflected is the darkest portion.

The pixel value profile generation unit 11 generates a profile in which the pixel value of each pixel belonging to the pixel array A and the position of each pixel are associated. This profile is referred to as a pixel value profile. The pixel value profile generation unit 11 generates a pixel value profile which is a profile indicating the relevance between the position of each pixel in the pixel array crossing the contour of the subject and the lung field and a corresponding pixel value.

Figure 4:
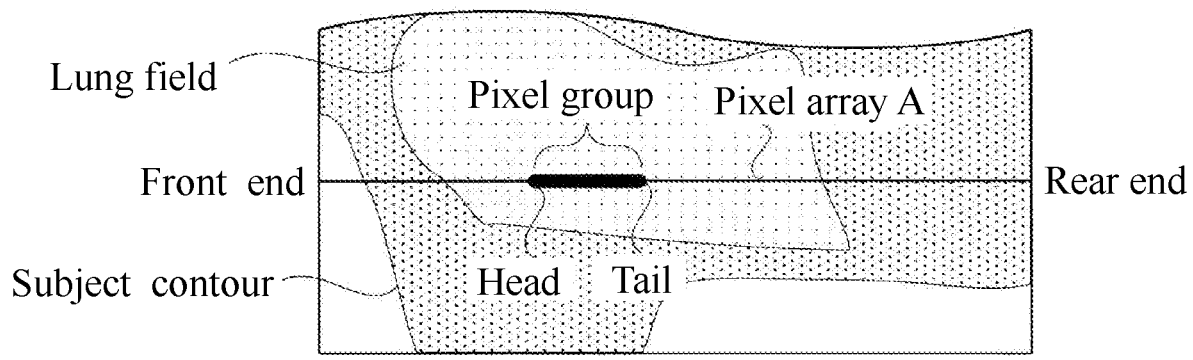
FIG. 4 is a schematic diagram illustrating moving average profile generation processing according to the first embodiment.

FIG. 4 illustrates the operation of the moving average profile generation unit 12. The moving average profile generation unit 12 generates a new profile different from the pixel value profile for the pixel array A designated by the pixel value profile generation unit 11. That is, the moving average profile generation unit 12 sets a pixel group on the pixel array A and generates a profile in which an average value of pixel values of pixels belonging to the pixel group and the position of the pixel group are associated. This profile will be referred to as a moving average profile. The pixel group is constituted by a predetermined number of pixels belonging to the pixel array A and arranged consecutively.

The shoulder side end of the pixel array A is defined as a front end, and the waist side end of the pixel array A is defined as a rear end. The boundary (contour of the subject) between the subject image and the air region in the original image P0 is positioned on the front end side of the pixel array A. The pixel group has a head facing the front end side of the pixel array A and a tail facing the rear end side of the pixel array A.

Figure 5:
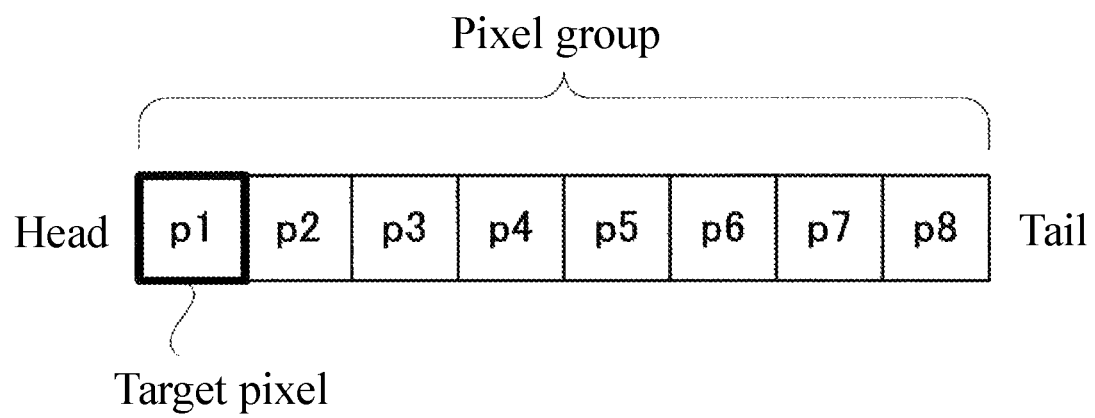
FIG. 5 is a schematic diagram illustrating the moving average profile generation processing according to the first embodiment.

FIG. 5 illustrates the details of the structure of the pixel group. In the example shown in FIG. 5, the pixel group is composed of eight pieces of the pixel p1 to the pixel p8 arranged in series. The pixel p1 positioned at the head of this pixel group is a pixel referred to as a target pixel and is a pixel representing the position of the pixel group on the original image P0. The pixel group is treated as being existed at the position of the target pixel on the original image P0.

Figure 6:
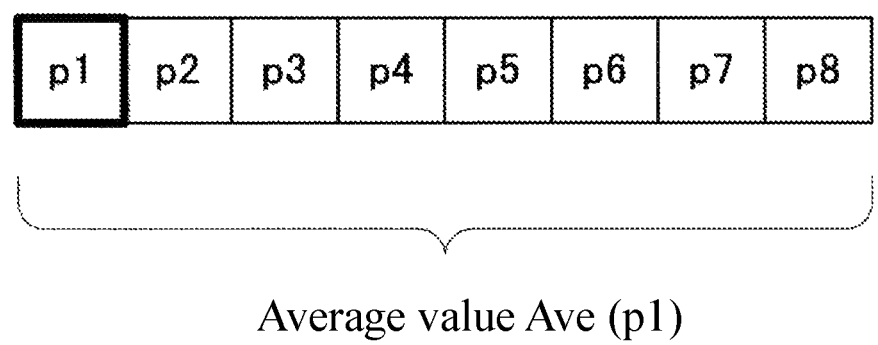
FIG. 6 is a schematic diagram illustrating the moving average profile generation processing according to the first embodiment.

FIG. 6 illustrates how the moving average profile generation unit 12 calculates the average value of the pixel group. The moving average profile generation unit 12 calculates the average value Ave by averaging the pixel values of the eight pieces of the pixel p1 to the pixel p8 constituting the pixel group. The average value Ave indicates the average value of the pixels in the pixel group, but since the position of the pixel group is defined based on the target pixel, the average value Ave can be considered to be a value related to the target pixel p1. Therefore, this average value can be expressed as a function Ave (p1).

Figure 7:
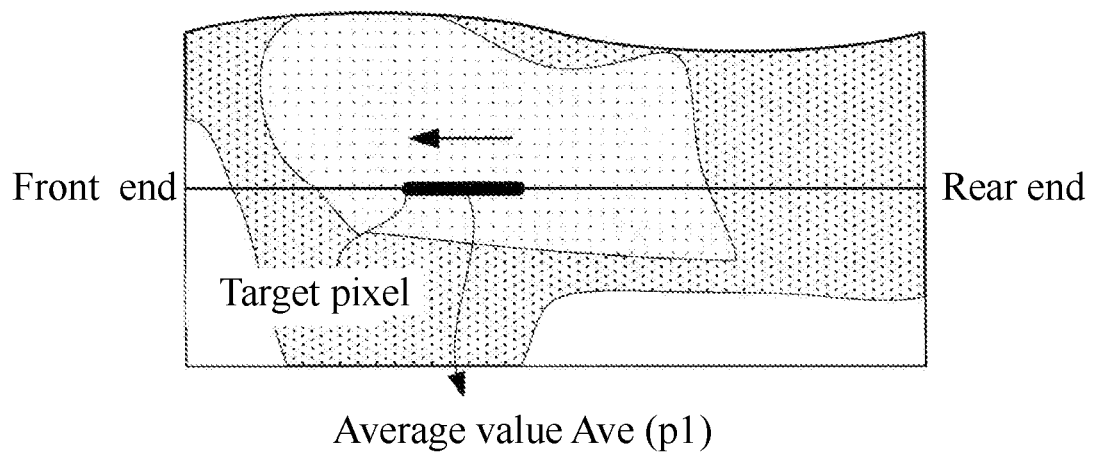
FIG. 7 is a schematic diagram illustrating the moving average profile generation processing according to the first embodiment.

FIG. 7 illustrates how the moving average profile generation unit 12 calculates the average value Ave (p1) while changing the position of the pixel group on the pixel array A. The calculation of this average value is executed while moving the pixel group in the direction from the rear end of the pixel array A to the front end thereof as indicated by the arrow in the figure. By this operation, the moving average of the pixel value on the pixel array A is calculated. This calculation of this average value is not required to be executed over the entire pixel array A. It is sufficient to execute the calculation from the center of the pixel array A to the front end thereof. This is because this section assuredly contains the contour of the subject positioned at the shoulder portion of the subject to be found. The moving average profile generation unit 12 generates a moving average profile while moving the pixel group from the rear end of the pixel array to the front end thereof.

Figure 8:
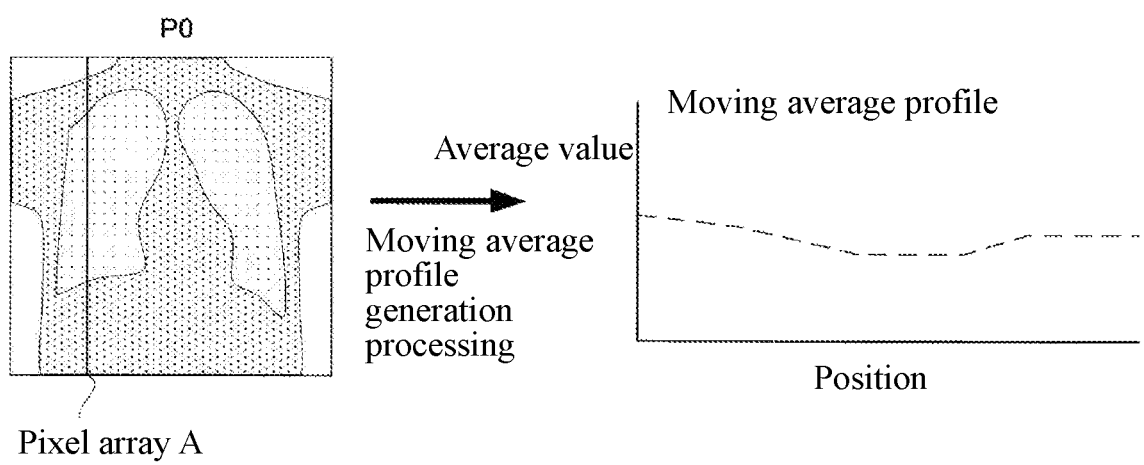
FIG. 8 is a schematic diagram illustrating the moving average profile generation processing according to the first embodiment.

FIG. 8 shows how the moving average profile generation unit 12 generates a profile associating the average value of the pixel group belonging to the pixel array A and the position of each pixel group. This profile will be referred to as a moving average profile. The position of each pixel group specifically denotes the position of each target pixel corresponding to each pixel group.

The moving average profile generation unit 12 generates a moving average profile indicating the relevance between the position of each target pixel and the moving average of the corresponding pixel value by setting the target pixel positioned at the head portion of the pixel group, calculating the moving average of the pixel values of the target pixel by averaging the pixel values of the pixels constituting the pixel group, thereafter sequentially calculating the moving average of the pixel values corresponding to the target pixels while moving the pixel group on the pixel array.

<Intersection Identification Unit 13>

The pixel value profile and the moving average profile generated by the generation units 11 and 12 respectively are sent to the intersection identification unit 13. The intersection identification unit 13 is configured to search the intersection of the profiles. This intersection represents the position of the contour of the subject reflected in the original image P0, and therefore this will be described.

Figure 9:
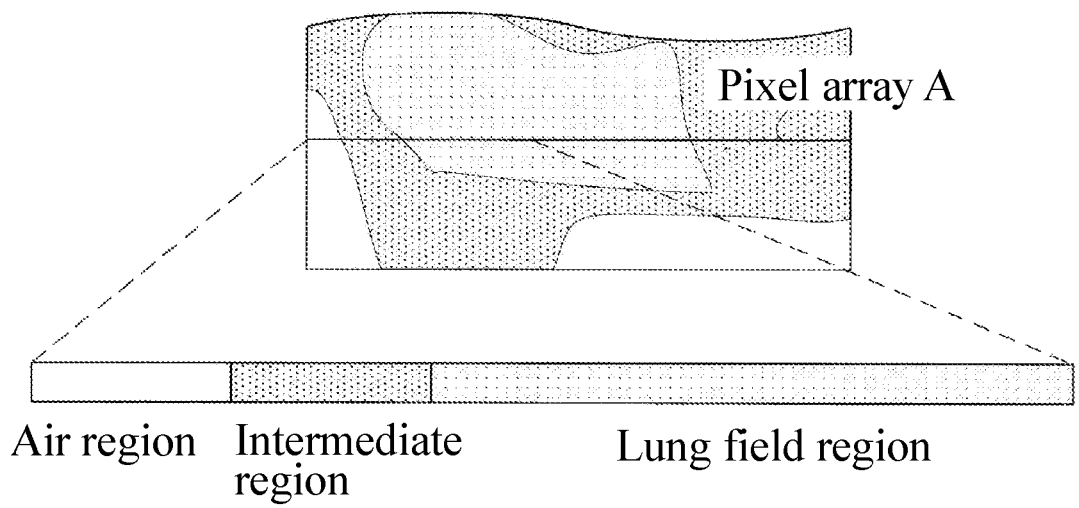
FIG. 9 is a schematic diagram illustrating intersection identification processing according to the first embodiment.

FIG. 9 specifically shows the arrangement configuration of the pixels on the pixel array A. The pixel array A includes three regions, i.e., an air region reflecting the air, a lung field region reflecting a lung filed of a subject, and an intermediate region reflecting a shoulder portion of a subject and positioned between the air region and the lung filed region. The air region is the brightest region on the pixel array A because the subject is not reflected. The lung field region is the next brightest region on the pixel array A because a vague lung of the subject is reflected. The intermediate region is the darkest region because the subject's clavicle and muscles are reflected. The purpose of the operation of the intersection identification unit 13 is to find the boundary between the air region and the intermediate region.

Figure 10:
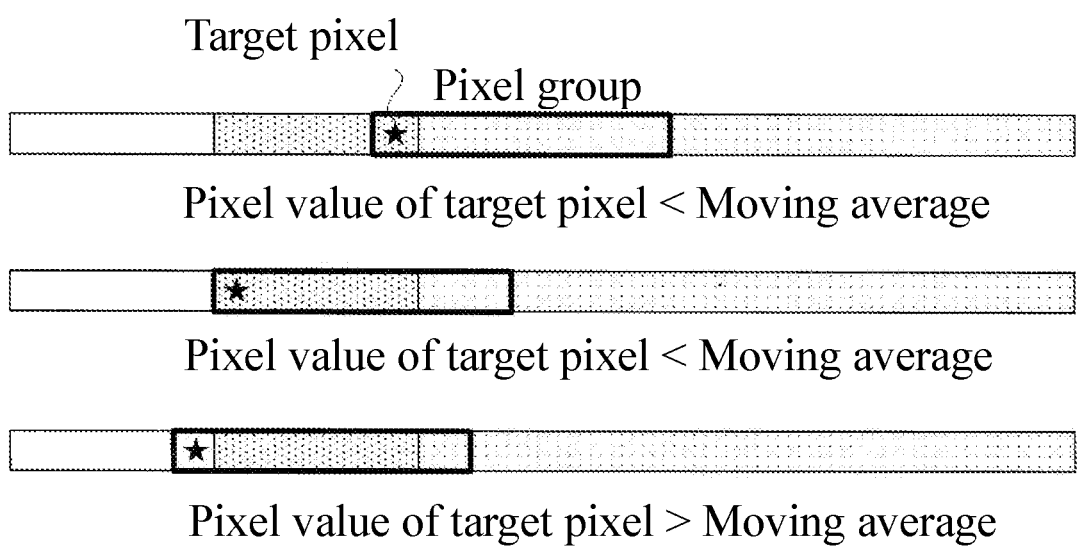
FIG. 10 is a schematic diagram illustrating the intersection identification processing according to the first embodiment.

FIG. 10 shows how the magnitude relation of the profiles changes with the position of the target pixel. In FIG. 10, the target pixel is indicated by an asterisk and the pixel group is indicated by a thick frame. The width of the pixel group is set so as to be longer than the width of the intermediate region. Therefore, the pixel group located at the position including the entire region of the intermediate region will protrude to the region next to the intermediate region.

First, as shown in the upper row in FIG. 10, a state is consider in which most of the pixel group is located in the lung field region and the head is located in the intermediate region. At this state, the pixel value is low because the target pixel is located in the dark intermediate region. On the other hand, the moving average is high. This is because most of the pixels constituting the pixel group are located in the bright lung field region. Therefore, in the case of the upper row in FIG. 10, the pixel value of the target pixel becomes smaller than the moving average.

Thereafter, the calculation of the moving average is continuously carried out while moving the pixel group towards the front end of the pixel array A. After a while, as shown in the middle row in FIG. 10, the target pixel reaches the end portion of the intermediate region. At this time, the pixel value is low because the target pixel is located in the dark intermediate region. On the other hand, the moving average gradually decreases but remains high. This is because the pixel group wider than the intermediate region is located such that the tail portion protrudes from the intermediate region and is located in the bright lung field region. Therefore, in the case of the middle row in FIG. 10, the pixel value of the target pixel remains smaller than the moving average.

As the calculation of the moving average is further continued, the target pixel reaches the air region as shown in the lower row in FIG. 10. At this time, the pixel value of the target pixel abruptly increases. On the other hand, the moving average does not change so much. This is because most of the pixels constituting the pixel group are located in the dark intermediate region. Therefore, in the case of the lower row in FIG. 10, the pixel value of the target pixel becomes larger than the moving average.

Therefore, to find the boundary between the air region and the intermediate region, it is only necessary to find the position where the magnitude relation between the pixel value of the target pixel and the moving average is reversed. Where this position comes on the pixel array A can be found by comparing the two profiles. That is, the intersection of the profiles appearing when the pixel value profile and the moving average profile are superimposed should be the boundary between the air region and the intermediate region. This is because the pixel value profile is nothing but related to the position of the pixel array A and the pixel value of the target pixel.

Figure 11:
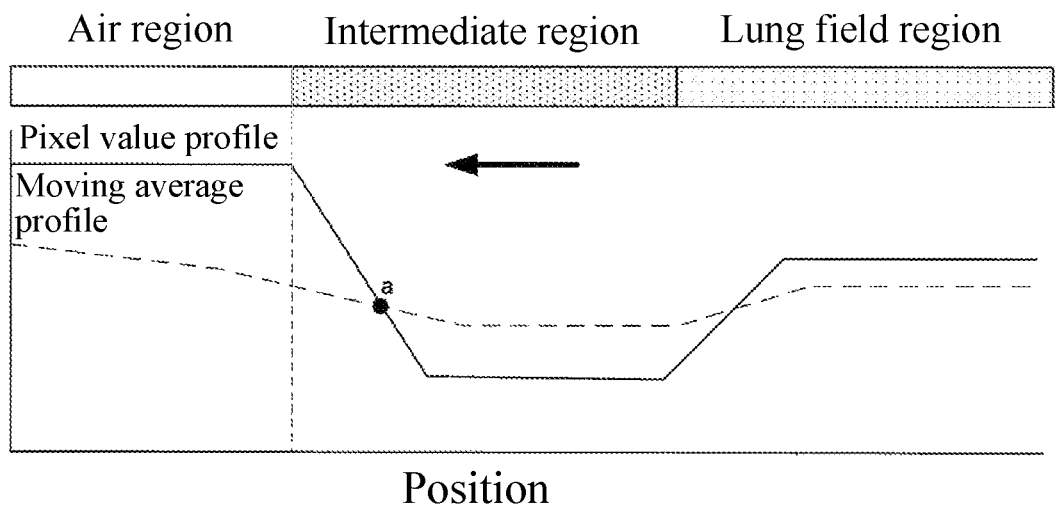
FIG. 11 is a schematic diagram illustrating the intersection identification processing according to the first embodiment.

FIG. 11 illustrates a state in which an actual pixel value profile and an actual moving average profile are superimposed based on this idea. In FIG. 11, the pixel value profile is indicated by a solid line, and the moving average profile is indicated by a broken line. The symbol "a" in FIG. 11 denotes the intersection in question.

Figure 12:
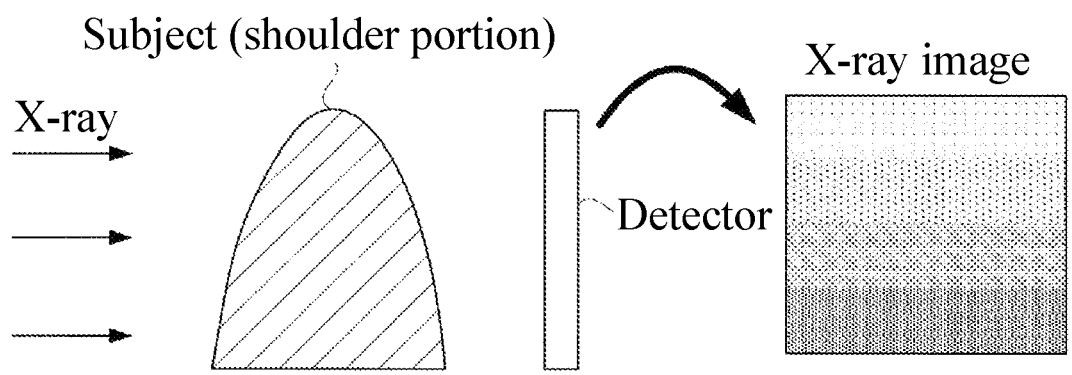
FIG. 12 is a schematic diagram for illustrating features of the intersection according to the first embodiment.

As will be understood from FIG. 11, strictly speaking, the intersection "a" is located in the intermediate region. That is, in fact, the description made with reference to FIG. 10 cannot be applied as it is. FIG. 12 describes the reason why such a phenomenon occurs. FIG. 12 illustrates how the X-ray image capturing is performed on the subject's shoulder portion. An X-ray is irradiated on the subject from the left side to the right side, passes through the subject's shoulder portion, and is detected by a detector. The ventral side of the subject is facing left and the dorsal side of the subject is facing right. The tip of the shoulder portion of the subject is thin, and therefore the obtained X-ray image becomes an image having a gradation which becomes brighter from the lower side to the upper side. That is, the vicinity of the boundary with the air region in the intermediate region of the pixel array A shown in FIG. 11 becomes gradually brighter toward the air region. This point is different from the simple model described with reference to FIG. 10 in handling the actual original image P0. For this reason, the intersection "a" does not appear at the boundary itself between the air region and the intermediate region but appears at a position slightly shifted toward the intermediate region.

Figure 13:
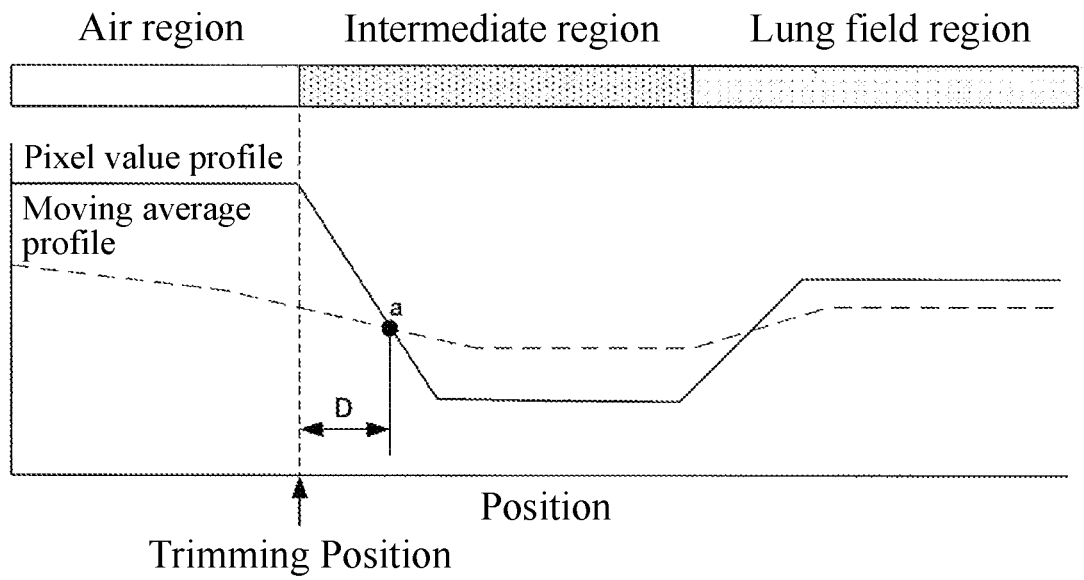
FIG. 13 is a schematic diagram for illustrating features of the intersection according to the first embodiment.

In view of such circumstances, as shown in FIG. 13, the configuration of the present invention is configured such that a position shifted from the intersection "a" in the direction toward the air region by a predetermined distance D is recognized as a boundary between the air region and the intermediate region. Such a recognition is executed by the trimming unit 14 which will be described later, so the details will be described later.

By the way, looking at FIG. 11, it should be noted that there are two intersections between the pixel value profile and the moving average profile. One of them is an intersection "a" which appears near the boundary between the air region and the intermediate region. The other is an intersection which appears around the boundary between the intermediate region and the lung field region. This means that the target boundary between the air region and the intermediate region cannot be identified without accurately distinguishing these two intersections.

The intersection identification unit 13 of the present invention is configured to search only an intersection where the profile reversal in which the pixel value profile lower than the average profile surpasses the moving average profile occurs when comparing the two profiles in the direction from the inside of the subject toward the air region (see the arrow in FIG. 11). Such an intersection is an intersection appearing around the boundary between the air region and the intermediate region that conform to the principle explained with reference to FIG. 10. Based on this principle, the intersection identification unit 13 distinguishes the boundary between the intermediate region and the lung field region and the boundary between the air region and the intermediate region.

<Relationship Between Intersection and Pacemaker Image>

The aforementioned operation of the intersection identification unit 13 is sufficient as a configuration for finding the boundary between the air region and the intermediate region in the X-ray image. However, in cases where a cardiac pacemaker is reflected in the X-ray image, it can happen that the intersection searched by the intersection identification unit 13 will not appear near the boundary between the air region and the intermediate region. The reason why such a phenomenon occurs will be described.

Figure 14:
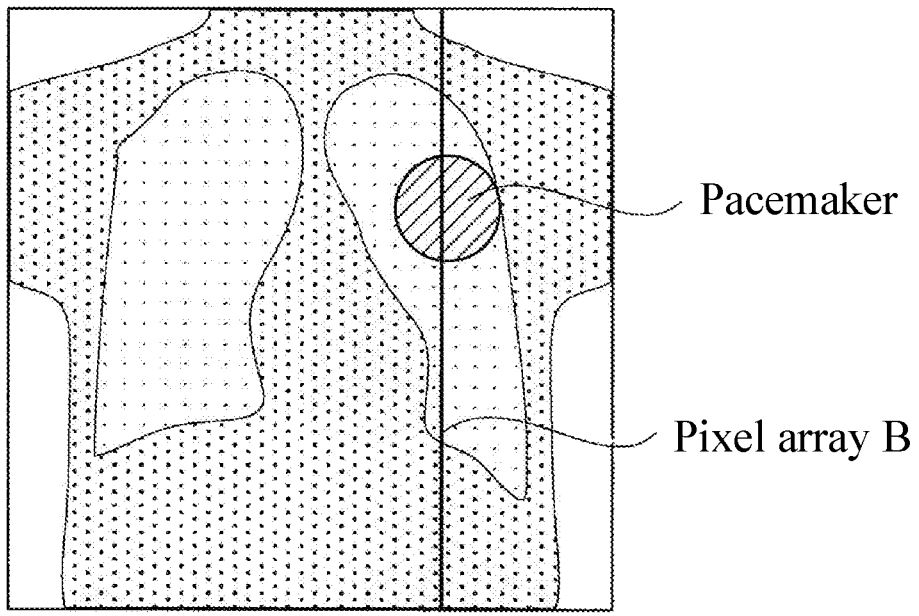
FIG. 14 is a schematic diagram illustrating the intersection identification processing according to the first embodiment.

As shown in FIG. 14, the pacemaker image is reflected at the position surrounded by the lung field. Therefore, both portions above and below the pacemaker image are lung fields. A case will be considered in which a pixel array B is set so as to cross the pacemaker image.

Figure 15:
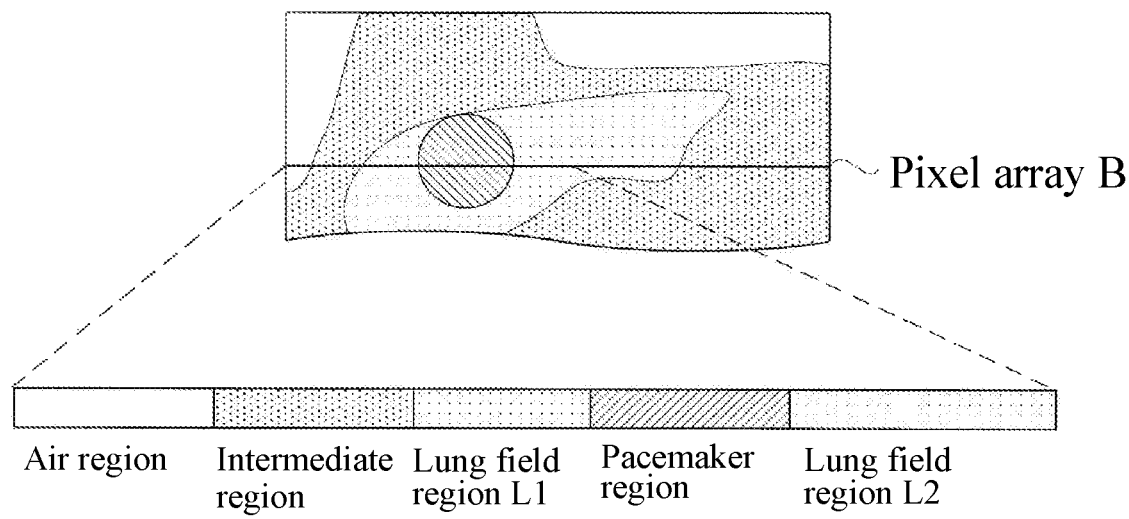
FIG. 15 is a schematic diagram for illustrating features of the intersection according to the first embodiment.

FIG. 15 specifically illustrates the configuration of the arrangement of the pixels on the pixel array B. The pixel array B includes, in the same manner as in FIG. 9, an air region reflecting the air, a lung field region reflecting a lung filed of a subject, and an intermediate region positioned between the air region and the lung field region and reflecting a shoulder portion of the subject. The difference from FIG. 9 is that the pacemaker region related to the pacemaker image is inserted in the lung field region. Arranging the regions on the pixel array B in the darkness order, the pacemaker region, the intermediate region, the lung field region, and the air region are arranged. The lung field region is divided by the pacemaker region. In the divided lung field region, the region fragment near the intermediate region is referred to as a lung field region L1, and the region fragment far from the intermediate region is referred to as a lung field region L2.

Figure 16:
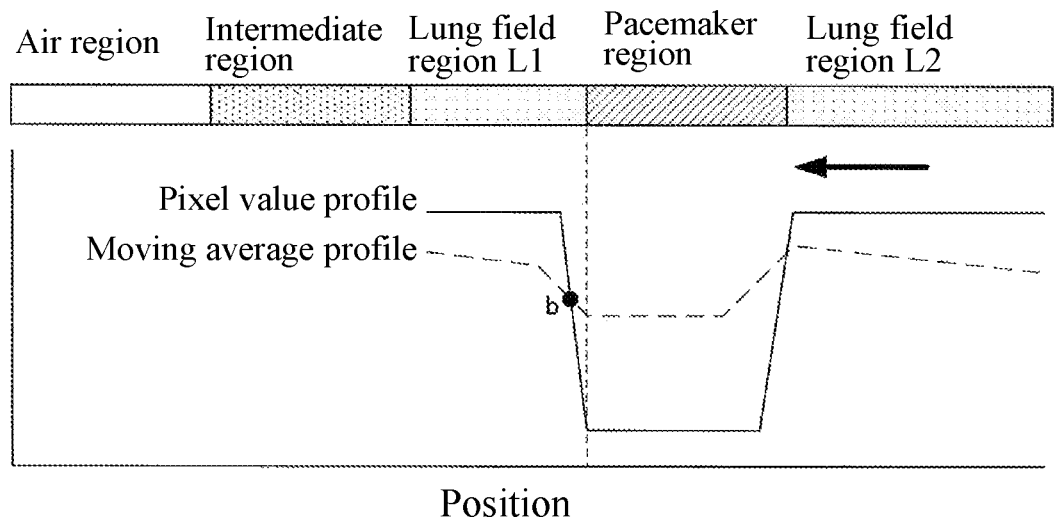
FIG. 16 is a schematic diagram for illustrating features of the intersection according to the first embodiment.

FIG. 16 illustrates the pixel value profile and the moving average profile related to the pixel array B in a superimposed manner. What is to be paid attention to is the boundary between the lung field region L1 and the pacemaker region. The pixel value profile in the pacemaker region is lower than the moving average profile. The pixel value profile shows a low value indicating the dark pacemaker region, while the moving average profile shows a high value due to the bright lung field region L2. However, the pixel value profile in the lung field region L1 is higher than the moving average profile. The pixel value profile shows a high value indicating the bright lung field region L1, while the moving average profile show a low value due to the dark pacemaker region. Therefore, at the boundary between the lung field region L1 and the pacemaker region, inversion occurs between the pixel value profile and the moving average profile.

When comparing two profiles in the direction from the inside of the subject toward the air region (see the arrow in FIG. 16), the profile inversion that the pixel value profile lower than the moving average profile surpasses the moving average profile occurs. Therefore, the intersection "b" satisfies all search conditions held by the intersection identification unit 13.

Under such circumstances, in cases where a pacemaker image is reflected in an X-ray image, there is a possibility that the intersection identification unit 13 searches the intersection "b" near the boundary between the lung field region L1 and the pacemaker region. Therefore, according to the present invention, it is configured to search an intersection for each of a plurality of pixel arrays different in position and recognizing an intersection located closest to the subject's head (on the air region side) among intersections as an intersection located near the boundary between the air region and the intermediate region to thereby prevent occurrence of the false recognition described above.

Figure 17:
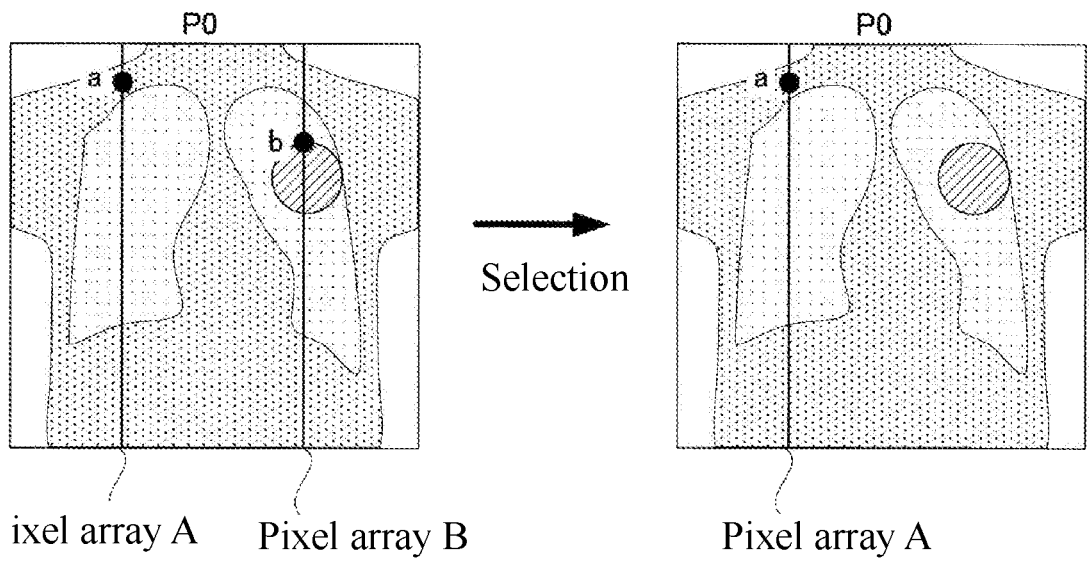
FIG. 17 is a schematic diagram illustrating the intersection identification processing according to the first embodiment.

FIG. 17 illustrates how the intersection identification unit 13 ultimately selects one intersection from multiple intersections. It is assumed that the intersection search was performed for a pixel array A and a pixel array B extending in parallel with each other, the intersection "a" was found for the pixel array A, and the intersection "b" was found for the pixel array B. The intersection identification unit 13 recognizes that the intersection "a" located on the side closer to the air region among intersections "a" and "b" is the final search result and treats that the intersection "b" is not found. The intersection identification unit 13 executes the search operation of the intersection on a plurality of pixel arrays extending in parallel with each other to thereby identify the intersection positioned closest to the front end side of the derived pixel array among intersections.

By performing such an operation, there does not occur that the intersection identification unit 13 recognizes the boundary between the lung field region L1 and the pacemaker region as the boundary between the air region and the intermediate region. This is because the boundary between the lung field region L1 and the pacemaker region should appear at a position far from the air region compared with the boundary between the air region and the intermediate region and will not become a selection target by the intersection identification unit 13.

<Relation between Intersection and Annotation Image>

Figure 28:
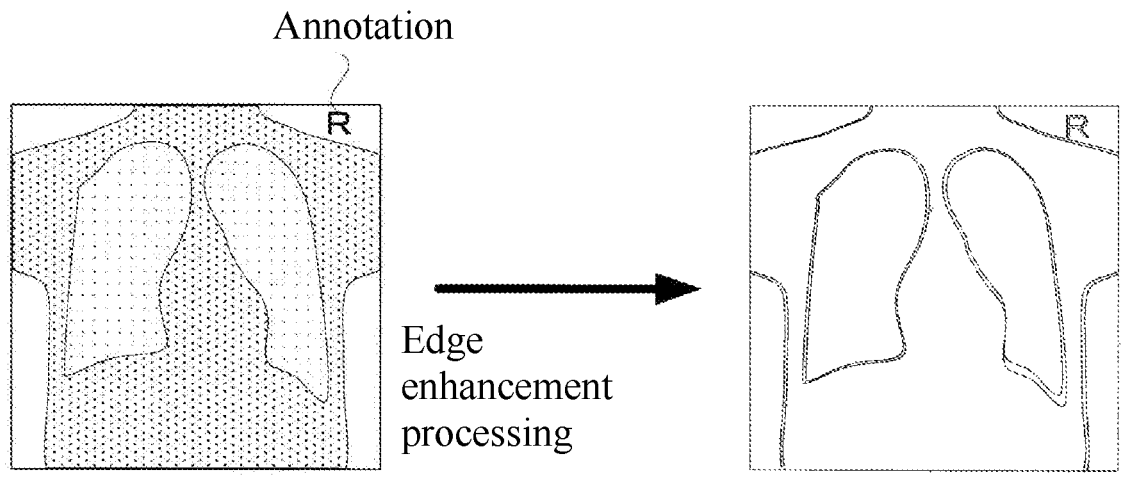
FIG. 28 is a schematic diagram illustrating the image processing of a conventional configuration.
Figure 29:
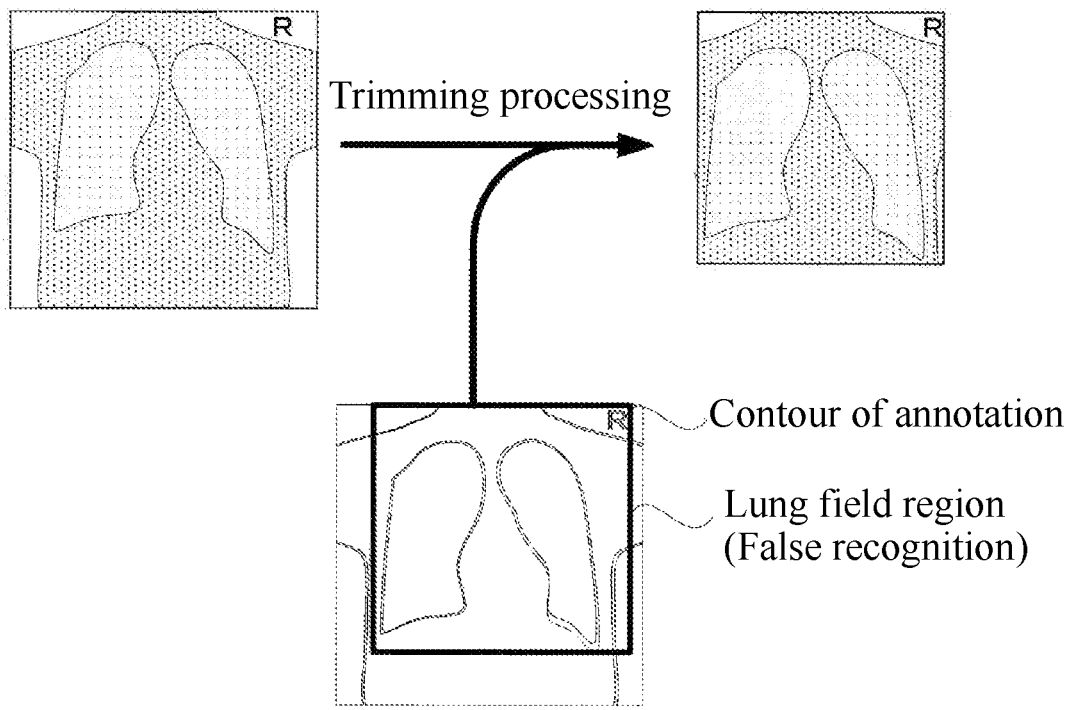
FIG. 29 is a schematic diagram illustrating the image processing of a conventional configuration.

Next, the relation between an intersection and an annotation will be explained. An annotation denotes a figure, such as, a letter "R" in FIG. 28, inserted in an air region of an X-ray image. There is a possibility that the inversion occurs between the pixel value profile and the moving average profile in the vicinity of this annotation. Therefore, it is considered that in cases where an annotation image is reflected in an X-ray image, the intersection of both profiles occurs at the boundary between the annotation image and the air region as described in FIG. 16 and this intersection become indistinguishable from the intersection occurred at the boundary between the air region and the intermediate region.

In this regard, for a certain pixel array A, it is supposed that there are a plurality of intersections where inversion of profiles occurs such that the pixel value profile lower than the moving average profile surpasses the moving average profile when comparing two profiles in the direction from the inside of the subject toward the air region (see the arrow in FIG. 11). In such a case, according to the present invention, it is configured such that the intersection identification unit 13 recognizes the intersection located closer to the lung field region among intersections as a search result for the pixel array A and processes as not having found any other intersections.

Figure 18:
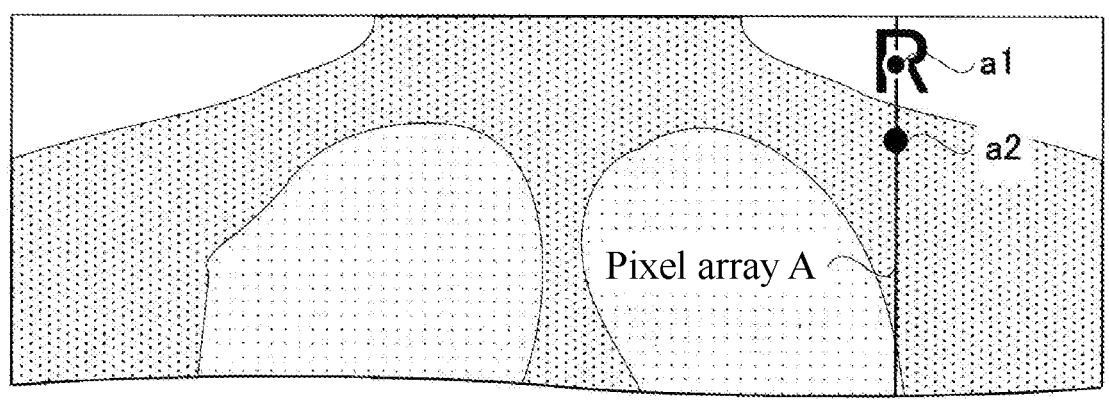
FIG. 18 is a schematic diagram for illustrating features of the intersection according to the first embodiment.

In the example of FIG. 18, since the intersection "a2" is closer to the lung field region than the intersection "a1", the intersection identification unit 13 recognizes the intersection "a2" as the intersection related to the pixel array A. By performing such an operation, the intersection identification unit 13 will not mistakenly recognize the boundary between the air region and the annotation as the boundary between the air region and the intermediate region. This is because that the boundary between the air region and the annotation should appear at a position far from the lung field region as compared with the boundary between the air region and the intermediate region and will not become a recognition target of the intersection identification unit 13. The intersection identification unit 13 searches the intersection located closest to the rear end side of the pixel array in cases where the intersection of both profiles appears on the same pixel array at a position where the pixel value profile surpasses the moving average profile in the direction from the rear end toward the front end in the pixel array.

As the actual operation of the intersection identification unit 13, it may be configured such that the comparison of both profiles is sequentially performed from the rear end of the pixel array A toward the front end thereof (in the direction from the lung field region toward the air region), the intersection found for the first time is recognized as the search result, and the search is completed at this point of time. Therefore, the intersection "a1" shown in FIG. 18 is not always found by the intersection identification unit 13. In the case of this configuration, the intersection identification unit 13 ends the operation without recognizing even the existence of the intersection "a1".

The intersection identification unit 13 identifies the intersection "a" based on such search condition and sends the position information of the intersection "a" in the pixel array A to the trimming unit 14.

<Operation of Trimming Unit 14>

The trimming unit 14 determines the position at which the trimming of the image is executed based on the position information of the sent intersection "a". That is, as shown in FIG. 13, the trimming unit 14 sets a position shifted from the position of the intersection "a" by a predetermined distance D in the direction from the intermediate region toward the air region as a trimming position. The trimming unit 14 operates by setting the position on the radiation image shifted from the intersection on the front end side of the pixel array by a predetermined width as the image cropping position.

Figure 19:
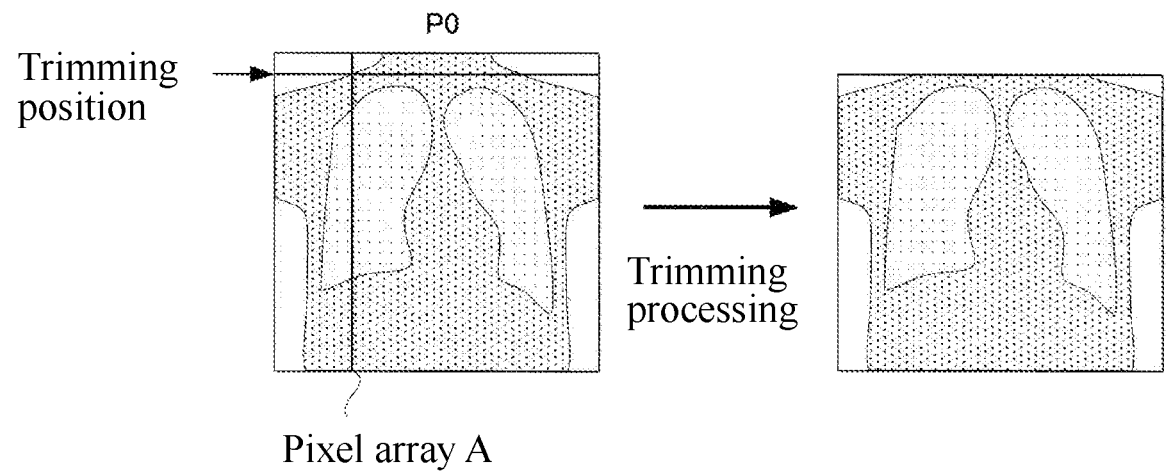
FIG. 19 is a schematic diagram for illustrating trimming processing according to the first embodiment.

FIG. 19 illustrates how the trimming processing of the original image P0 is actually executed based on the set trimming position. The trimming unit 14 recognizes the division line passing through the trimming position on the pixel array A and executes the trimming of the original image P0 so that the air region in the pixel array A is cut away on the division line. Note that the division line is orthogonal to the pixel array A.

Figure 20:
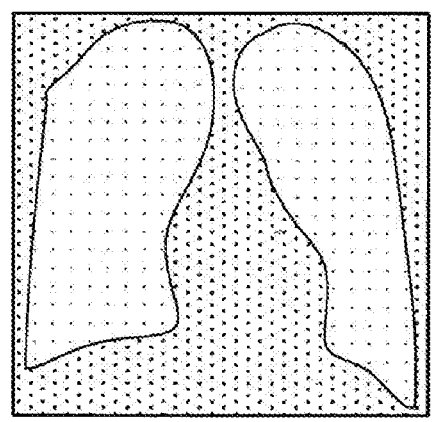
FIG. 20 is a schematic diagram illustrating a trimmed image according to the first embodiment.

FIG. 20 shows the result of the trimming operation performed on the top, bottom, left, and right of the original image P0. The trimming operation at this time may be carried out by the method according to the present invention described with reference to FIGS. 3 to 19 or by a conventional method. The image according to FIG. 20 is an image in a state in which the trimming operation has been completed. The image will be referred to as a trimmed image T. The trimming unit 14 performs trimming for extracting the lung field together with the peripheral portion from the radiation image by recognizing the position of the peripheral portion of the lung field based on the position of the contour of the subject based on the intersection searched.

Figure 25:
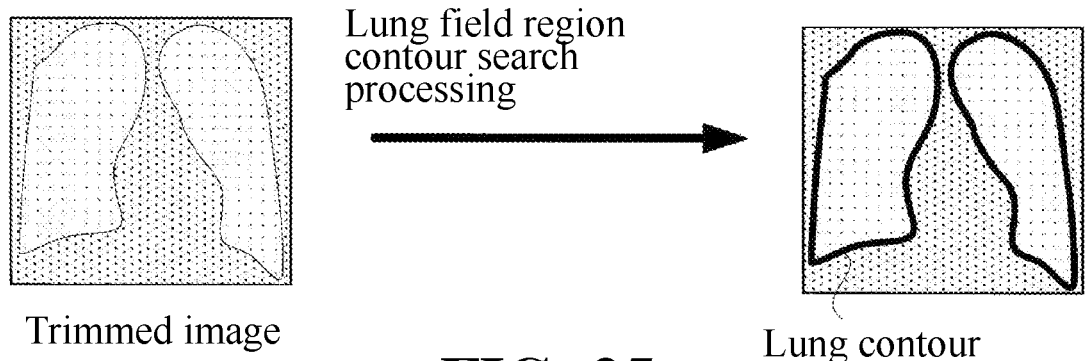
FIG. 25 is a schematic diagram illustrating the image processing of a conventional configuration.
Figure 26:
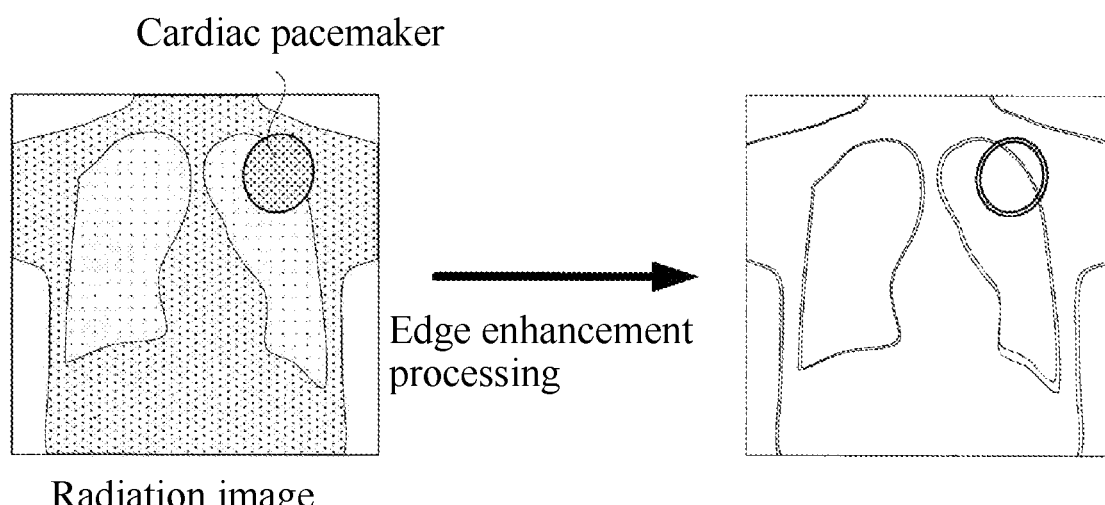
FIG. 26 is a schematic diagram illustrating the image processing of a conventional configuration.
Figure 27:
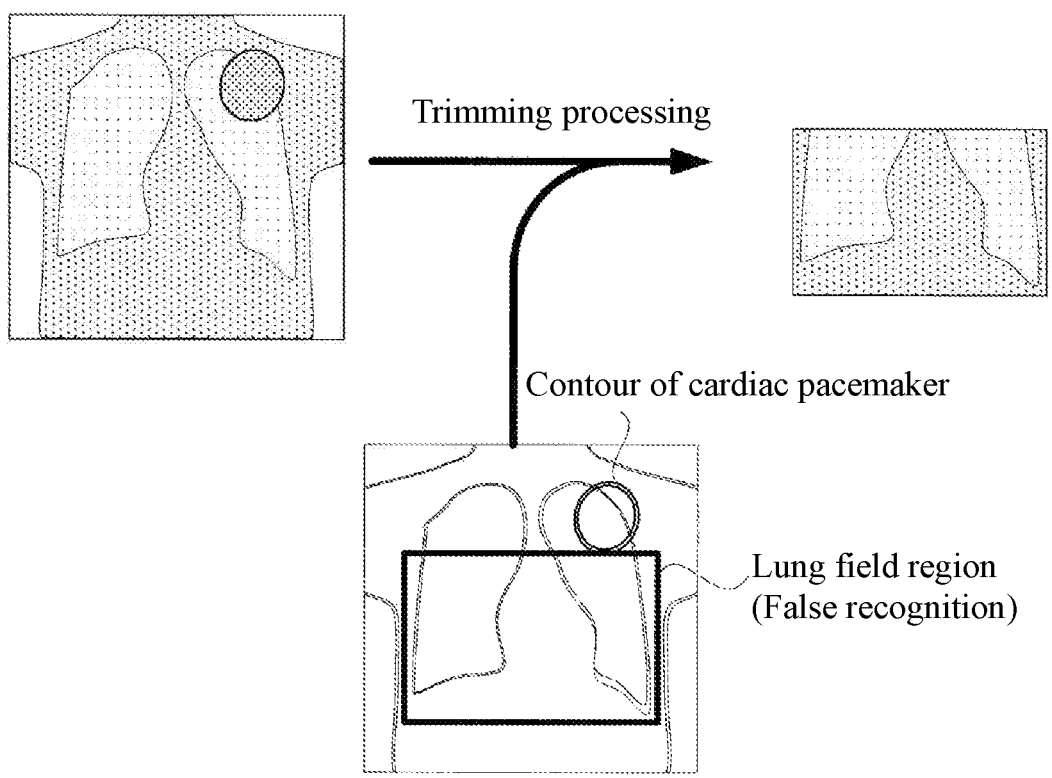
FIG. 27 is a schematic diagram illustrating the image processing of a conventional configuration.

The trimmed image T is sent to the lung field contour extraction unit 15. The lung field contour extraction unit 15 extracts the contour of the lung field reflected in the trimmed image T as described with reference to FIG. 25. The lung field contour extraction unit 15 extracts the contour of the lung field reflected in the trimmed image T generated by the trimming unit 14. The data indicating the contour of the lung field is sent to the lung field luminance adjustment unit 16. The lung field luminance adjustment unit 16 executes the luminance adjustment only on the lung field on the trimmed image T as described with reference to FIG. 25. With this operation, in the lung field, the contrasting density will be assuredly enhanced, resulting in improved visibility.

As described above, according to the present invention, it is possible to provide an image processing apparatus which can assuredly improve visibility of a lung field by assuredly recognizing a position of the lung field reflected in a radiation image. That is, according to the configuration of the present invention, it is provided with the intersection identification unit 13 configured to generate a pixel value profile which is a profile indicating the relevance between the position of each pixel in the pixel array crossing the contour of the subject and the lung field and the corresponding pixel value and a moving average profile which is a profile indicating the relevance between the position of each target pixel and the moving average of the corresponding pixel value, and search the intersection of both profiles located at the position where the pixel value profile surpasses the moving average profile from the direction from the rear end towards the front end in the pixel array (the direction from the lung field side to the contour side of the subject). This intersection is likely to indicate the position of the contour of the subject.

The present invention can accurately identify a contour of a subject even if an annotation is reflected in a radiation image. This is because the intersection identification unit 13 searches the intersection located closest to the rear end side of the pixel array among intersections that meet the condition. The contour of the subject is located on the rear end side of the pixel array than the annotation, and therefore it can be judged that the intersection located closest to the rear end side among intersections that meet the condition is related to the contour.

In the present invention, even if an image of a cardiac pacemaker is reflected in a radiation image, the contour of the subject can be accurately identified. This is because the intersection identification unit 13 executes the intersection search operation for a plurality of pixel arrays arranged in parallel with each other to acquire an intersection corresponding to each pixel array and identifies an intersection located closest to the front end side of the pixel array. There are a pixel array crossing the image of the cardiac pacemaker and a pixel array not crossing the image of the cardiac pacemaker. From the pixel array crossing the pacemaker image, an intersection is found at the boundary between the lung field and the pacemaker image. From the pixel array not crossing the image of the cardiac pacemaker, an intersection is found at the position of the contour of the subject. There are an intersection located on the front end side and an intersection located on the rear end side. Since the image of the cardiac pacemaker is located closer to the rear end side of the pixel array than the contour of the subject, the intersection located on the rear end side is considered to be located at the boundary between the lung field and the pacemaker image. According to the present invention, since the intersection located closest to the front end side of the pixel array among intersections operates as an intersection indicating the position of the contour of the subject, there is no false recognition of the boundary between the lung field and the image of the cardiac pacemaker as the contour of the subject.

When the contour of the subject is extracted, the image processing for extracting the entire lung field from the radiation image can be assuredly performed, which in turn can assuredly improve the visibility of the lung field.

The present invention is not limited to the aforementioned embodiment, but can be modified as follows.

(1) According to the aforementioned embodiment, the moving average profile generation unit 12 generates a moving average profile for the entire area of the pixel array A, but the present invention is not limited to this configuration. For the rear end side of the pixel array A, there is no need to generate a moving average profile. It is sufficient to start the generating of the moving average profile from the position where the entire region of the pixel group belongs to the lung field region. In addition, the generation of the moving average profile may be started from the position where the pixel group crosses the intermediate region and the lung field region. By performing such an operation, the operational cost of the moving average profile generation unit 12 can be reduced.

Figure 21:
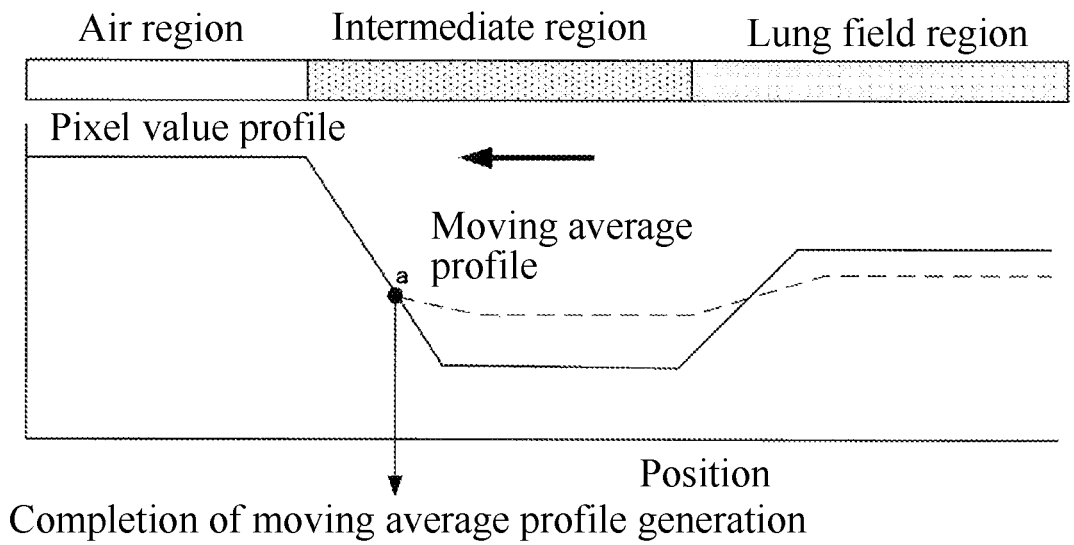
FIG. 21 is a schematic diagram illustrating image processing of a conventional configuration.
Figure 22:
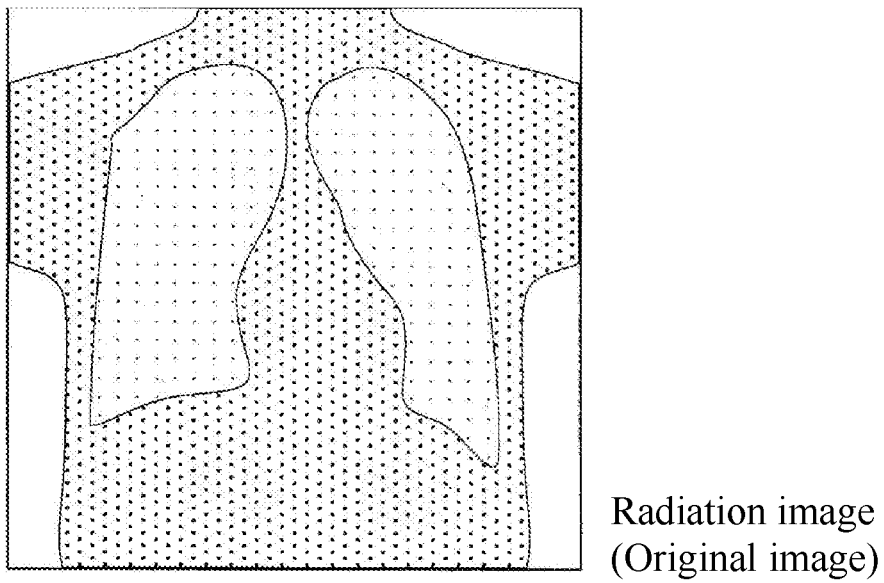
FIG. 22 is a schematic diagram illustrating the image processing of a conventional configuration.
Figure 23:
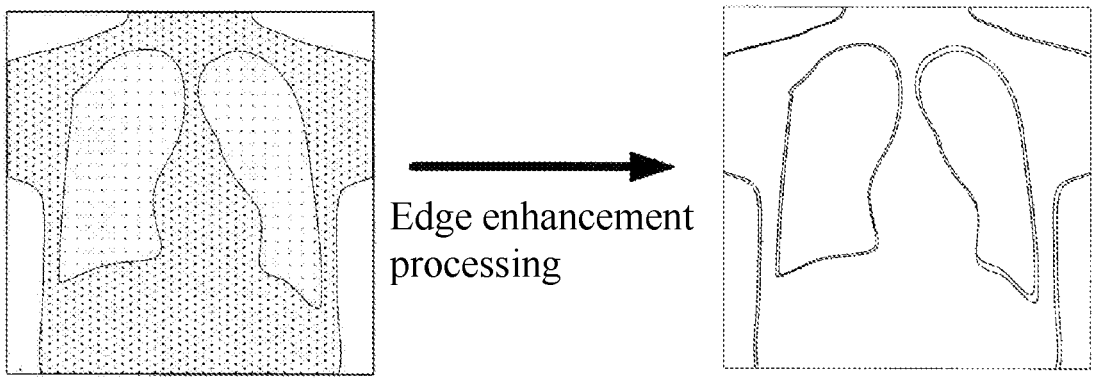
FIG. 23 is a schematic diagram illustrating the image processing of a conventional configuration.
Figure 24:
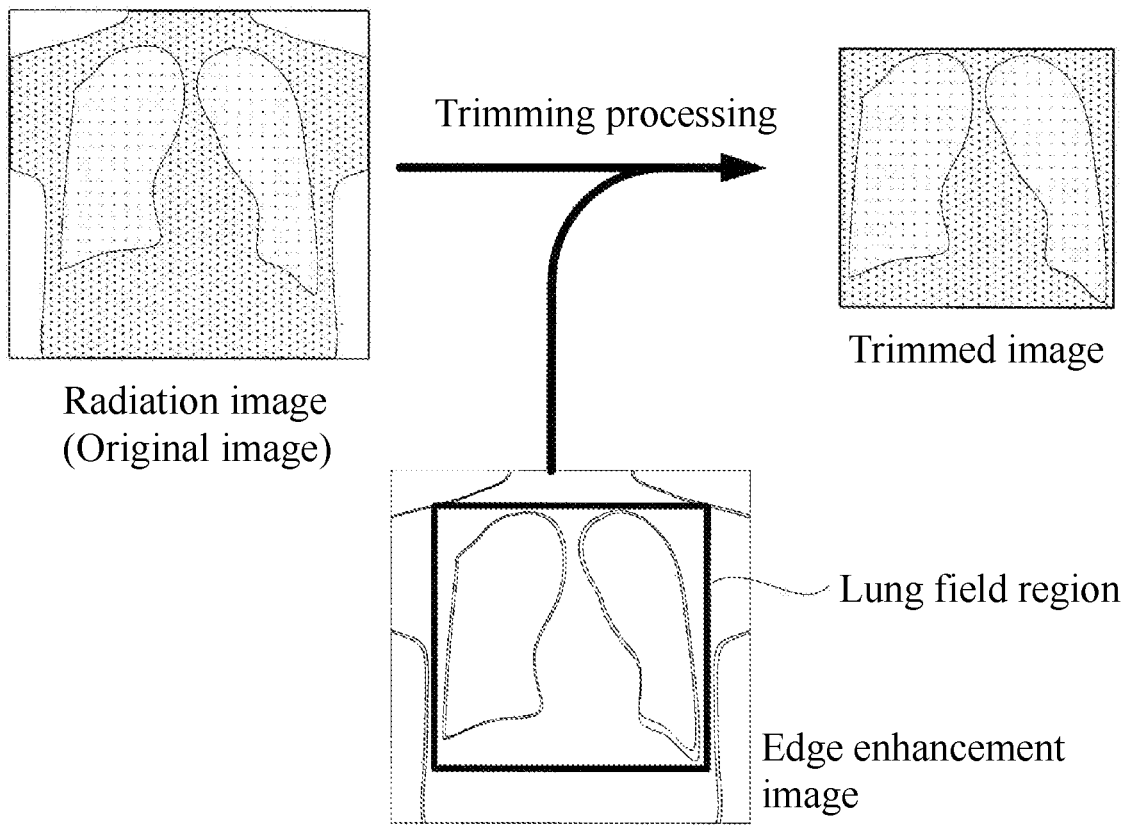
FIG. 24 is a schematic diagram illustrating the image processing of a conventional configuration.

(2) According to the aforementioned embodiment, the moving average profile generation unit 12 generates a moving average profile for the entire area of the pixel array A, but the present invention is not limited to this configuration. For the front end side of the pixel array A, there is no need to generate a moving average profile. FIG. 21 illustrates the operation of the moving average profile generation unit 12 at this time. The moving average profile generation unit 12 calculates the moving average while moving the pixel group in the direction of the arrow from the inside of the subject toward the air region, and the calculated moving average is sequentially sent to the intersection identification unit 13. When the intersection identification unit 13 searches the intersection "a", it gives a feedback to the moving average profile generation unit 12 and stops the calculating of the moving average. By performing such an operation, the operational cost of the moving average profile generation unit 12 can be reduced. The intersection identification unit 13 of this modified embodiment repeatedly executes the search of the intersection every time a moving average of pixel value is calculated, and the moving average profile generation unit 12 terminates the generation of the moving average profile when the intersection identification unit 13 completed the search of the intersection.

(3) The image processing apparatus according to the present invention can also be realized by executing the following processing. That is, a software (program) for realizing the functions of the aforementioned embodiments is supplied to a system or an apparatus via a network or various storage media, a computer (or CPU, MPU, etc.) of the system or an apparatus reads out the program, and this processing is executed.

(4) The image processing apparatus according to the present invention can be mounted on a radiation image capturing apparatus.

DESCRIPTION OF REFERENCE SYMBOLS

11: pixel value profile generation unit (pixel value profile generation means)

12: moving average profile generation unit (moving average profile generation means)

13: intersection identification unit (intersection identification means)

14: trimming unit (trimming means)

15: lung field contour extraction unit (lung field contour extraction means)

The invention claimed is:

1. An image processing apparatus for applying a luminance adjustment to a lung field corresponding portion of a radiation image reflecting a contour of a subject, comprising:

a pixel value profile generation means configured to generate a pixel value profile which is a profile indicating relevance between a position of each pixel in a pixel array crossing the contour of the subject and the lung field and a corresponding pixel value;

a moving average profile generation means configured to generate a moving average profile which is a profile indicating relevance between a position of each target pixel and a moving average of a corresponding pixel value by setting a pixel group having a head of the pixel array facing a front end which is a contour side of the subject and a tail of the pixel array facing a rear end side which is a lung field side, setting the target pixel among the pixel group positioned at a head portion, calculating the moving average of the pixel value of the target pixel by averaging the pixel values of pixels constituting the pixel group, and thereafter successively calculating the moving average of the pixel value corresponding to the target pixel while moving the pixel group on the pixel array;

an intersection identification means configured to identify an intersection located closest to a front end side of the pixel array among intersections different in derived pixel array by searching an intersection located closest to the rear end side of the pixel array among intersections of the two profiles appearing at a position where the pixel value profile surpasses the moving average profile from a direction from a rear end of the pixel array to a front end of the pixel array, and executing a search operation for a plurality of pixel arrays arranged in parallel with each other;

a trimming means configured to execute trimming for extracting the lung field together with a peripheral portion thereof from the radiation image by recognizing a position of the peripheral portion of the lung field based on a position of the contour of the subject based on a searched intersection; and a lung field contour extraction means configured to extract a contour of the lung field reflected in a trimmed image generated by the trimming means.

2. The image processing apparatus as recited in claim 1, wherein the trimming means operates by setting a position on the radiation image shifted from the intersection toward the front end side of the pixel array by a predetermined width to an image cutting out position.

3. The image processing apparatus as recited in claim 1, wherein the moving average profile generation means generates the moving average profile while moving the pixel group from the rear end to the front end of the pixel array.

4. The image processing apparatus as recited in claim 3, wherein the intersection identification means repeatedly executes an intersection search every time the intersection identification means calculates the moving average of the pixel value, and the moving average profile generation means ends generation of the moving average profile when the intersection identification means completes the intersection searching.

5. A program, stored in non-transitory computer readable medium, causing a computer to function as each means of the image processing apparatus as recited in claim 1.

6. A radiation image capturing apparatus equipped with the image processing apparatus as recited in claim 1.

* * * * *